United States Patent
Iijima et al.

(10) Patent No.: US 6,258,857 B1
(45) Date of Patent: Jul. 10, 2001

(54) INTERNAL LIQUID COMPOSITION CONTAINED AS INTERNAL LIQUID IN A RELEASING CONTAINER AND RELEASING CONTAINER PRODUCT

(75) Inventors: Kazuo Iijima; Haruhisa Uenoyama; Takuya Sakai, all of Osaka (JP)

(73) Assignee: Kyowa Industrial Co., Ltd., Osaka (JP)

( * ) Notice: Subject to any disclaimer, the term of this patent is extended or adjusted under 35 U.S.C. 154(b) by 0 days.

(21) Appl. No.: 09/244,088

(22) Filed: Feb. 4, 1999

(51) Int. Cl.$^7$ ............... A61K 7/46; A61K 9/18; C09K 3/30
(52) U.S. Cl. ............... 516/1; 424/46; 424/421; 512/4; 514/919
(58) Field of Search ............... 516/1; 424/46, 424/421; 514/919; 512/4

(56) References Cited

U.S. PATENT DOCUMENTS

| | | | |
|---|---|---|---|
| 4,164,561 | * 8/1979 | Hautmann | 424/46 X |
| 4,464,317 | * 8/1984 | Thies et al. | 424/421 X |
| 4,613,500 | * 9/1986 | Suzuki et al. | 424/46 X |
| 5,122,418 | * 6/1992 | Nakane et al. | 424/46 X |
| 5,510,109 | * 4/1996 | Tomioka et al. | 424/421 |
| 5,582,815 | * 12/1996 | Appino et al. | 424/46 X |
| 5,635,214 | * 6/1997 | Ponchon et al. | 424/421 X |
| 5,679,324 | * 10/1997 | Lisboa et al. | 514/937 X |

FOREIGN PATENT DOCUMENTS

| | | | |
|---|---|---|---|
| 987301 | 3/1965 | (GB) . | |
| 2018593 | * 10/1979 | (GB) | 424/421 |
| 7216104 | 5/1995 | (JP) . | |
| 9157107 | 6/1997 | (JP) . | |
| 9208406 | 8/1997 | (JP) . | |

* cited by examiner

Primary Examiner—Richard D. Lovering
(74) Attorney, Agent, or Firm—Birch, Stewart, Kolasch & Birch, LLP

(57) ABSTRACT

The invention relates to an internal liquid composition contained in a releasing container such as an aerosol container, and a releasing container product containing such composition. The following three types are proposed as the composition. The first type is a blending of inorganic porous fine particles carrying a chemical, disperse solution, acrylic acid polymer, and alkali. The second type is a blending of inorganic porous fine particles carrying a chemical, disperse solution, and synthetic resin fine particles. The third type is a blending of inorganic porous fine particles carrying a chemical, disperse solution, acrylic acid polymer, alkali, and synthetic resin fine particles. As inorganic porous fine particles, for example, silicic anhydride porous fine particles may be used. The chemical to be carried by the inorganic porous fine particles includes perfume, insect repellent, agricultural chemical, deodorant, plant extract, ultraviolet blocker, antioxidant, antipruritic, hair growth promoter, vitamin, antiperspirant, sunburn remedy, antiseptic, moisturizer, styptic, oil, and others. As disperse solution, water, alcohol, ether and other organic solvents may be used.

6 Claims, 4 Drawing Sheets

INTERNAL LIQUID COMPOSITION CONTAINED AS INTERNAL LIQUID IN A RELEASING CONTAINER AND RELEASING CONTAINER PRODUCT

BACKGROUND OF THE INVENTION

The present invention relates to (1) a composition contained in a releasing container such as an aerosol container or pump type releasing container, and used as being released from such releasing container, and (2) a releasing container product containing such composition.

As general forms of use of water-soluble or water-insoluble chemicals (for instance, perfume or insect repellent composition for humans or animals), they are widely sold as aerosol products or pump type releasing container products. In the form of an aerosol product, a container having an injection valve is packed with a releasing composition such as a chemical, and a high pressure propellant, and by opening the injection valve, the chemical is injected out of the container together with the high pressure propellant. In the form of a pump type a releasing container product, a container having a releasing pump is packed with a releasing composition such as a chemical, and the chemical is injected out of the container by manually manipulating the releasing pump.

In blending of the content of the aerosol product, for example, an aerosol can of 90 to 160 ml in capacity is filled with 2 to 15 wt. % of chemical such as perfume or repellent, 25 to 35 wt. % of isopropyl alcohol, and 60 wt. % of chlorofluorocarbon, and in its method of use, by pressing a button, the injection valve is opened, and it is sprayed and used in proper positions by the pressure of chlorofluorocarbon.

However, when sprayed or applied in the human living space by using the spray of such conventional blending, in the environments of high temperature in summer, for example, the chemical is evaporated soon, and its effect does not last longer than several hours. If prepared in an emulsion form, it is evaporated soon, too.

Such problems can be solved by carrying the chemical on inorganic porous fine particles, sealing in the container together with other liquid, and releasing. The chemical held in the pores of the inorganic porous fine particles is gradually evaporated after being sprayed, and the chemical effect lasts for a relatively long time.

The inorganic porous fine particles are solid, and form a powder phase when gathered together, and therefore it is necessary to disperse them uniformly in the container. However, when inorganic porous fine particles are dispersed in the conventional liquid, although they are dispersed right after stirring, they sediment as the time passes, and are separate from the liquid if transferred by the pressure of propellant or pump, and the dispersion is not uniform.

On the other hand, Japanese Patent Application laid open No. 7-126104 discloses, as an insect repellent composition for humans, use of silicic anhydride with a specific surface area of 500 $m^2/g$ or more, as the composition not whitened, long in repellent efficacy, and excellent in feel of use. Japanese Patent Application laid open No. 9-208406 discloses the art of defining the pore volume at 1 ml/g or less, mean pore size at 100 angstroms or less, and specific surface area at less than 500 $m^2/g$, as the condition of silicic anhydride fine particles to be used for achieving the same purpose as the insect repellent composition. Moreover, Japanese Patent Application laid open No. 9-157107 discloses, as aerosol for insect repellent, use of a composition containing hydrocarbon of low boiling point, with an injection amount per 3 seconds of 2.0 to 5 ml, and oil absorption amount of powder of 250 ml/100 g or less. Incidentally, UK Patent Specification No. 987,301 "Aerosol Compositions" discloses an art for obtaining an aerosol product by filling a pressure-proof can with powder having drug effects such as an antiperspirant and deodorant, together with alcohol, dispersant, and silicic anhydride fine particles as crude solution, and further adding propellants such as chlorofluorocarbon or LPG.

It is hence a first object of the invention to carry a chemical on inorganic porous fine particles, enhance the sustained-release effect of the chemical, and disperse the inorganic porous fine particles as the powder phase (solid phase) more uniformly in a disperse solution. That is, it is intended to enhance the dispersion performance of the inorganic porous fine particles.

It is another object of the invention to make it easy to maintain the disperse state of the inorganic porous fine particles in the disperse solution as powder phase (solid phase) when sealed into the aerosol container together with the propellant. More specifically, a stock solution completed as liquid of favorable dispersion is contained in an aerosol can (container), and a valve is attached, and when filled with a propellant, the dispersion in the aerosol composition may be impaired due to the characteristic of the propellant. For example, it is often a problem of pH in the case of carbon dioxide, or it is a problem due to compatibility of stock solution and propellant in the case of liquefied gas. Therefore, desired active ingredients may not be used and, it is hard to find substitutes, or it takes a tremendous time to search the disperse solution, active agent or solvent. It is hence a second object of the invention to suppress lowering of dispersion performance in the container as far as possible, by minimizing the effects from propellant or other contents, regarding the dispersion performance of inorganic porous fine particles. That is, it is intended to prevent lowering of the dispersion performance of inorganic porous fine particles due to propellant.

Other problems include a problem of re-dispersion of the powder phase. However the dispersion performance may be improved by achieving the first and second objects of the invention, the true specific gravity of the powder phase (solid phase) of the disperse phase is, for example, about 2.15, whereas the specific gravity of the disperse solution to be used is, for example, about 0.82. Therefore, when the product is let stand for 10 days, 20 days, or several months, the solid phase settles in the bottom of the liquid. It depends on the art of the engineer how to disperse it again easily, by such simple operation as to hold and shake the container one or two times. That is, it requires various experiments in selection and combination of dispersant, moisturizer and active agent, adjustment of liquid viscosity, powder particle size, bulk specific gravity, surface treatment, and others. It is hence a third object of the invention to re-disperse inorganic porous fine particles smoothly.

Another problem is to emphasize the merits the of powder phase, that is, the silicic anhydride porous fine particles, and to conceal the demerits. Advantages of inorganic porous fine particles are to extend the drug effect by carrying the active ingredients, prolong the retention time of the inorganic porous fine particles by developing on the skin surface, and avoid sticky feel on the skin surface. However, if the inorganic porous fine particles are used excessively, due to stiffness of the inorganic porous fine particles, a stiff feel is expressed, and dry or smooth feel is lost. It is hence a fourth object of the invention to improve the touch on the skin surface if applied on the skin, that is, to give a dry and smooth feel of use.

Moreover, when the inorganic porous fine particles are dried, they appear white, and a strange feel is given visually. It is hence a fifth object of the invention not to give a strange feel visually, that is, not to whiten.

BRIEF SUMMARY OF THE INVENTION

The present inventors made various investigations in order to solve the above problems, and hence discovered the following three compositions, as the internal liquid composition to be contained in an aerosol container as the internal liquid in a releasing container.

The first internal liquid composition of the invention comprises inorganic porous fine particles carrying a chemical, disperse solution, acrylic acid polymer, and alkali.

The second internal liquid composition of the invention comprises inorganic porous fine particles carrying a chemical, disperse solution, and synthetic resin fine particles.

The third internal liquid composition of the invention comprises inorganic porous fine particles carrying a chemical, disperse solution, acrylic acid polymer, alkali, and synthetic resin fine particles.

The inventors further invented releasing container products containing these first, second and third internal liquid compositions.

The first internal liquid composition of the invention comprises inorganic porous fine particles carrying a chemical, disperse solution, acrylic acid polymer, and alkali. In this internal liquid composition, by the thickening action and pH adjustment obtained by the acrylic acid polymer and alkali, the inorganic porous fine particles carrying the chemical can be uniformly dispersed in the disperse solution. Moreover, when the disperse solution is evaporated after releasing onto the object, a film of the acrylic acid polymer can be formed on the surface of inorganic porous fine particles, and dissipation of the carried chemical is delayed, so that the sustained-release effect can be enhanced.

The second internal liquid composition of the invention comprises inorganic porous fine particles carrying a chemical, disperse solution, and synthetic resin fine particles. The inventors discovered that the dispersion and re-dispersion performance of inorganic porous fine particles can be enhanced and that lowering of dispersion performance of inorganic porous fine particles due to propellant can be prevented by introducing fine particles of other material (that is, synthetic resin particles) capable of preventing collision among these fine particles in the group of inorganic porous fine particles such as group of silicic anhydride fine particles, and thereby completed the second internal liquid composition of the invention.

More specifically, in the course of various experiments about the first internal liquid composition of the invention, the inventors noticed that the re-dispersion of the inorganic porous fine particles was lowered as the content of carbon dioxide as propellant in the aerosol product was increased. A superficial cause is changes of pH of the internal liquid due to filling with carbon dioxide. The relation between the pH changes and lowering re-dispersion is estimated as follows. That is, the electric charge on the surface of fine particles is considered to have an action to prevent collision between fine particles. This is because fine particles of positive (+) and negative (−) polarity attract each other by the electrostatic repulsion of electric charge of same polarity.

For example, when silicic anhydride fine particles are used as inorganic porous fine particles, the acidity of the internal solution is increased by filling with carbon dioxide and the concentration of hydroxide ions in the internal solution is lowered in the disperse solution of water or alcohol, and silicic ions are also decreased. When the concentration of the remaining silicic ions is lowered, the electric charge on the surface of fine particles decreases. As a result, the electric charge on fine particles is insufficient, and collision between fine particles cannot be prevented.

Accordingly, when both silicic anhydride fine particles and synthetic resin fine particles are coexistent in the disperse solution, frictional charging hardly occurs between the both fine particles, and since charging of the two is both negative (−), so that collision between fine particles can be prevented. At this time, the particle size of the synthetic resin fine particles is preferred to be same as the particle size of silicic hydride porous fine particles, or larger than the particle size of silicic hydride porous fine particles. That is, by decreasing the particle size of silicic hydride porous fine particles which are more likely to have effects of pH, and increasing the particle size of organic synthetic resin fine particles which are less likely to have effects of electric charge by pH, the behavior between fine particles by electric charge is dominant, and therefore it is considered that collision between fine particles can be prevented by the electric charge.

The third internal liquid composition of the invention comprises inorganic porous fine particles carrying a chemical, disperse solution, acrylic acid polymer, alkali, surface active agent, and synthetic resin fine particles, and it exhibits the actions of both first and second internal liquid compositions.

DETAILED DESCRIPTION OF THE PREFERRED EMBODIMENTS

Figure 1:
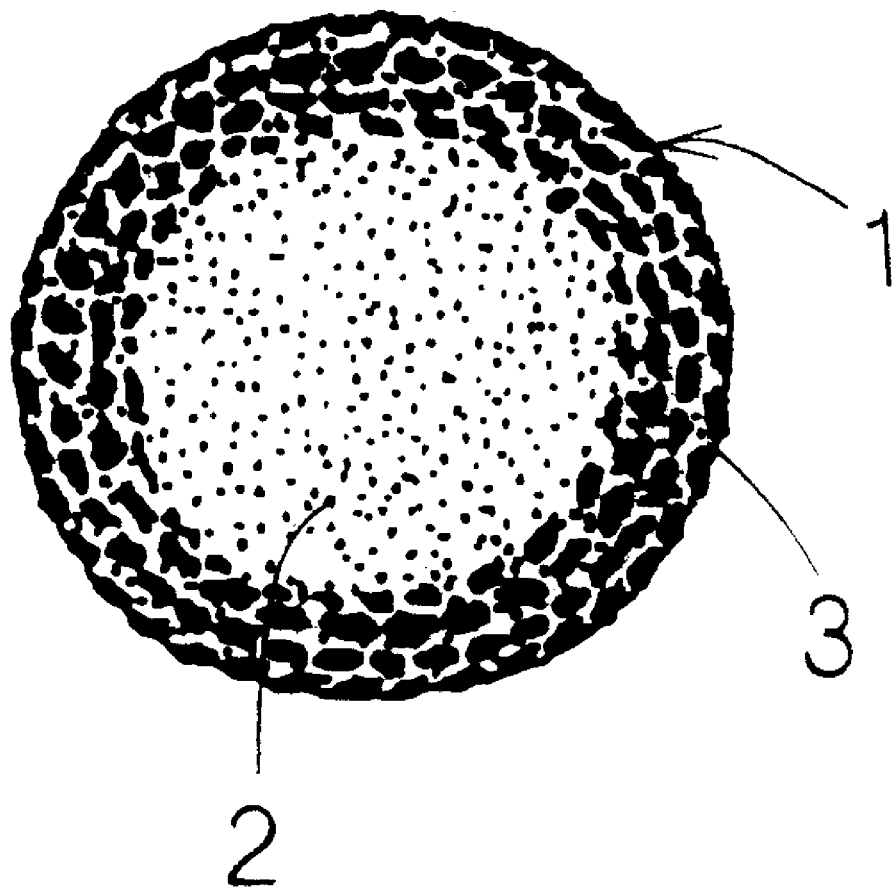
FIG. 1 is a sectional view showing an example of hollow inorganic porous fine particles enveloping a chemical of the invention.

The internal liquid composition of the invention is a liquid contained in a container having a releasing mechanism, and released by the releasing mechanism, and it may be composed either of liquid alone, or by blending solid (mostly, in a form of powder or fine particles) in the liquid.

Typical examples of releasing means include the aerosol mechanism and pump spray mechanism.

The aerosol mechanism is intended to inject the internal liquid from an outlet of the aerosol container by the pressure of a propellant contained in the aerosol container, such as aerosol can, together with the internal liquid. The released form of the internal liquid include fog, mousse, stream, paste, and others, and it may be injected or applied in an optimum pattern depending on the purpose. It is an aerosol product that the internal liquid and propellant are contained together in an aerosol container such as aerosol can in a form of a product.

The pump spray mechanism is used in a spray product, and has a spraying mechanism. The spray product, also called the pump product, is a product of sucking up the internal liquid by vertical action of finger by using a pump-operated sprayer, pressurizing, and spraying like a fog. For example, the internal liquid is sucked up by vertical motion of finger, and sprayed. When a pump spray is used in the product, it is a spray product.

The internal liquid composition of the invention includes the first, second and third compositions mentioned above, and, first of all, common matters to these internal liquid compositions are described.

In these internal liquid compositions, the chemical is blended in a form of being carried on inorganic porous fine particles. The type of the chemical is not particularly limited, and any material suited to the application of the release container product may be used, and in particular any compound that is likely to be evaporated in the environments of 10 to 100 deg. C, more preferably, 25 to 50 deg. C may be used.

Practical examples of the chemical include perfume, repellent, agricultural chemical, deodorant, plant extract, ultraviolet blocker, antioxidant, antipruritic, hair growth promoter, vitamin, antiperspirant, sunburn remedy, antiseptic, moisturizer, styptic, oil, and others, and one type or two or more types thereof may be used by blending depending on the purpose of use.

The perfume is a substance giving off a fragrance, not harmful for the human health. It is, for example, classified into natural perfume and synthetic perfume, and the natural perfume is further divided into plant perfume and animal perfume. Mixing these perfumes, a blend perfume may be also used in the invention. If unstable in heat, it may be carried on the inorganic porous fine particles of the invention.

Examples of natural perfume include acacia oil, ilang-ilang oil, fennel oil, wintergreen, onion oil, orange oil, cassia oil, cashew oil, chamomile oil, mustard oil, grapefruit oil, clove oil, coriander oil, sandalwood oil, cedarwood oil, citronella oil, jasmine oil, ginger oil, calamus oil, gingergrass oil, cinnamon oil, narcissus oil, spearmint oil, sage oil, geranium oil, thyme oil, nutmeg oil, pine oil, menthol oil, rose oil, hyacinth oil, peppermint oil, mint oil, eucalyptus oil, lime oil, lavender oil, lemongrass oil, lemon oil, rosewood oil, rosemary oil, rose oil, lovage oil, and others, and one or two or more natural perfumes may be used.

Examples of synthetic perfume include alpha-pinene, beta-pinene, d-limonene, citronellal, heliotropin, vanillin, camphor, benzophenone, muscone, musk, linalol oxide, cineol, benzoic acid, and others, but the perfumes usable in the invention are not limited to these examples alone.

The agricultural chemical is a pesticide for repelling or killing animals, insects, mites, nematodes, microorganisms and others. Examples are bactericide, insecticide, acaricide, nematocide, etc.

The bactericide is a chemical for killing various bacteria and fungi such as plant pathogens. Specific examples of bactericide include dithiocarbamate, organic sulfur compound, organic phosphorus compound, copper compound, antibiotics, etc. One or two or more kinds of the examples of the bactericide may be used.

The insecticide is a chemical for killing cockroach, mosquito, flea, mite, other sanitary pests and agricultural pests. Specific examples of insecticide include organic phosphorus insecticide (dichlorvos, cynofos, o-ethyl-o-phenyl phosphothionate, malathion, parathion, etc.), carbamate insecticide (1-naphthyl-N-methyl carbamate, isoprocarb, etc.), organic halogen insecticide (DDT, benzahexachloride, eldrin, aldrin, dieldrin, etc.), nicotines (nicotine, nornicotine, etc.), fluoroacetic amide, pyrethroids (pyrethrin, arethrin, etc.), plant derivative refined oil (cineol, dill oil, Japanese mint oil, eucalyptus oil, turpentine oil, etc.), boric acid, and others. One or two or more kinds of these examples of insecticide may be used.

The acaricide is a chemical for killing mites such as acarus and acarid. Specific examples of acaricide include kerosene, prochlonol, chlorobenzilate, chloropropylate, phenysobromolate, chlorofenson, tetradifon, propargito, pinapacryl, tricyclohexyltin hydroxide, phenbutastannic oxide, chinothiomate, amitraz, benzomate, polynactions, lavender oil, Melissa oil, peppermint oil, salvia oil, rosemary oil, and others. One or two or more kinds of these examples of acaricide may be used.

The nematocide is a chemical for killing nematodes, such as pine wood nematode, root-knot nematode, and root lesion nematode. Specific examples of nematocide include mesulfenfos, morantel tartate, chloropicrin, mixture of 2,3-dichloropropane and 1,3-dichloropropene, 1,2-dibromomethane, methyl isocyanate, and others. One or two or more kinds of these examples of nematocide may be used.

The antibacterial compound is, unlike the bactericide, a chemical for suppressing the growth of bacteria and fungi without killing them. Specific examples of antibacterial compound include methylparaben, ethylparaben, propylparaben, vanillin, cinnamic aldehyde, p-hydroxybenzoic ester, d-limonene, ethyl alcohol, camphor, phenyl oxide, p-dichlorobenzene, dimethyl fumarate, hinoki oil, hiba arborvitae oil, Taiwanese hinoki oil, cassia oil, dill oil, lemon oil, citronella oil, clove oil, thyme oil, linalol, trans-pinocarbeol, p-isopropyl cyclohexanol, campherenic aldehyde, gamma-decalactone, gamma-undecalactone, and others. One or two or more kinds of these examples of antibacterial compound may be used.

The repellent is a chemical for keeping animals, sanitary pests, agricultural pests, or insects away from humans, animals or other specific individuals. Specific examples of repellent include lemongrass oil, lemongrass, synthesized musk, cinnamic aldehyde, pine oil, eugenol, turpinenol, wood vinegar, vanillin, acetoxy phenyl butane, hexanal, geranyl formate, alpha, beta-pinene, limonene, safrole, anetol, anisaldehyde, gamma-lactone, 1,8-cineol, naphthalene, angelica, cyclic terpene alcohol, menthol, N,N-diethyl-m-toluamide, ethyl omethone, isothionate, cresol, spices (pepper, capsicum, mint, perilla, clove, etc.), vanilla, nonyl lactone, citrile, linalol, 2-butoxy ethanol, bisether, cyclohexanone, isophorone, spearmint oil, green leaf alcohol, cinnamon alcohol, methyl nonyl ketone, methyl phenyl ketone, camphor, citral, eucalyptol, allyl isocyanate, capsaicin, cycloheximide, and others. One or two or more kinds of these examples of repellent may be used.

The deodorant is for eliminating the cause of unpleasant smell by aromatizing, masking or neutralizing it. Specific examples of deodorant by aromatizing include rose oil, lily oil, fragrant olive oil, jasmine oil, lemon oil, gardenia oil, mint oil, violet oil, and other perfumes. Specific examples of deodorant by masking include, among the perfumes, cinnamic aldehyde, vanillin, heliotropin, coumarin, carbon, canaphor, boneol, and others. Specific examples of deodorant by neutralizing include terebinth oil, clove oil, cinnamon oil, cedar oil, orange oil, lemon oil, orange peel oil, and others. Besides, flavonoid and others may be also used. One or two or more kinds of these examples of deodorant may be used.

The plant extract has various drug effects, and includes aloe extract, chamomile extract, orange extract, seaweed extract, watercress extract, archangel extract, Saint-John's-wort extract, perilla extract, coptis rhizome extract, prune extract, raspberry extract, ivy extract, cinchona extract, gardenia extract, mulberry extract, geranium herb extract, burdock extract, mixed fruit extract, mixed plant extract, comfreyextract, peonyroot extract, and others. One or two or more kinds of these examples of plant extract may be used.

The ultraviolet blocker is used for absorbing ultraviolet rays in wavelength of 200 to 400 nm, preventing harmful actions on human body or cosmetics, and further preventing sunburn of the skin and deterioration of cosmetics by the blocker. Specific examples include 2-hydroxy-4-methoxy benzophenone, 2-hydroxy-4-methoxy-2'-carboxy benzophenone, 5-chloro-2-hydroxy benzophenone, 2,4-hydroxy benzophenone, 2-oxy-5-methoxy acetophenone, and other benzophenones. Other examples are benzoic ester, including ethyl-p-glucosyl imide benzoate, glucosyl-p-amino benzoate, salicylate ester, p-octyl phenoyl salicylate, and phenyl salicylate. One or two or more kinds of these examples of ultraviolet blocker may be used.

The antioxidant is a chemical for preventing oxidation and degeneration of substance by oxygen. Specific examples of antioxidant include nordihydroguaiaretic acid, guaiacum, gallic propyl, butyl hydroxy anisol, dibutyl hydroxy toluene, alpha-tocopherol (vitamin E), and others. Other examples are water-soluble antioxidants, including sodium sulfite, ascorbic acid, sodium pyrosulfite, isoascorbic acid, thiosorbitol, cysteine hydrochloride, thioglycolic acid, and sodium thiosulfate. One or two or more kinds of these examples of antioxidant may be used.

The antipruritic is for preventing itch by local anesthesia and fresh stimulating action, and specific examples include camphor, thymol, menthol, polyoxy ethylene lauryl ether, antihistaminic, aminobenzoic ethyl, and others. One or two or more kinds of these examples of antipruritic may be used.

The hair growth promoter is for encouraging growth of hair by permeating deeply into roots of hair, promoting blood flow in the hair papilla, and stimulating division of mother cells of hair, and specific examples include cantharide tincture, capsicum tincture, ginger tincture, cefalantin, lecithin, hinokitiol, photosensitive agent No. 301, estrogen, pantothenic acid, swertia herb extract, glycyrrhizin, and others. One or two or more kinds of these examples of hair growth promoter may be used.

The vitamin is supplied as nutrition to the human body, and water-soluble and fat-soluble vitamins can be used. Specific examples of water-soluble vitamin include vitamin B group such as vitamin B1, vitamin B2, vitamin B6 and vitamin B12, and vitamin C, and others. Specific examples of fat-soluble vitamin include vitamin A, vitamin E, vitamin D, and others. One or two or more kinds of these examples of vitamin may be used.

The antiperspirant has an action to suppress perspiration, and specific examples include aluminum chloride, allantoin, chlorohydroxy aluminum, aluminum sulfate, alum, aluminum chlorohydroxide, and others. One or two or more kinds of these examples of antiperspirant may be used.

The sunburn remedy is to prevent sunburn of the human body, and contains ultraviolet absorbent and ultraviolet scattering agent. Specific examples of ultraviolet scattering agent include zinc oxide, titanium oxide, and others. One or two or more kinds of these examples of ultraviolet scattering agent may be used.

The antiseptic is used for the purpose of storage without deterioration of quality of the chemical by suppressing growth of microorganisms, and specific examples include benzoic acid, salicylic acid, dehydroacetic acid, sorbic acid, boric acid, chloroxylenol, resorcin, paraoxy benzoic ester, phenoxy ethanol, thymol, hinokitiol, thioxolone, benzalkonium chloride, benzethonium chloride, lauryl di(aminoethyl) glycine, chlorobutanol, and others. One or two or more kinds of these examples of antiseptic may be used.

The moisturizer has an action of keeping the skin warm and moist, and specific examples include glycerin, propylene glycol, sorbit, 1,3-butylene glycol, d1-pyrrolidone carboxylic acid, sodium lactate, and others. One or two or more kinds of these examples of moisturizer may be used.

The styptic is contained in cosmetics to make the skin tight and firm, and specific examples include citric acid, tartaric acid, lactic acid, aluminum chloride, aluminum sulfate, potassium sulfate, allantoin chlorohydroxy aluminum, allantoin chlorodihydroxy aluminum, aluminum phenol sulfonic acid, paraphenol sulfonic zinc, zinc sulfate, aluminum chlorohydroxide, and others. One or two or more kinds of these examples of styptic may be used.

The oil, when used in cosmetics, is to provide the skin with flexibility, cleanliness, rubbing effect, moisture keeping effect, gloss and other actions.

Examples are oils, fats, wax, higher fatty acid, hydrocarbon, and others, and specific examples are almond oil, olive oil, camellia oil, castor oil, wood wax, palm oil, lanolin, cetanol, liquid lanolin, paraffin, vaseline, squalane, oleic acid, lauric acid hexyl, myristic acid isopropyl, palmitic acid isopropyl, myristic acid octyl dodecyl, and others. One or two or more kinds of these examples of oil may be used.

These chemicals are only examples, and other compound may be also used.

The following may be used as inorganic porous fine particles for impregnating or carrying these chemicals.

The inorganic porous fine particles are porous substance made from an inorganic compound, and its shape is varied, including an amorphous shape, and in particular a nearly spherical shape is preferred.

The content of the inorganic porous fine particles in the internal liquid composition may be varied appropriately, but is preferred to be in a range of 0.01 to 60 wt. %.

Examples of inorganic compound include carbonate, silicate, phosphate and sulfate of alkaline earth metal, metal oxide, metal hydroxide, other metal silicate, or other metal carbonate, etc.

Specific examples of carbonate of alkaline earth metal include calcium carbonate, barium carbonate, magnesium carbonate, and others. Examples of silicate of alkaline earth metal include calcium silicate, barium silicate, magnesium silicate, and others. Examples of phosphate of alkaline earth metal include calcium phosphate, barium phosphate, magnesium phosphate, and others. Examples of sulfate of alkaline earth metal include calcium sulfate, barium sulfate, magnesium sulfate, and others.

Examples of metal oxide include silica, titanium oxide, iron oxide, cobalt oxide, zinc oxide, nickel oxide, manganese oxide, aluminum oxide, and others. Examples of metal hydroxide include iron hydroxide, nickel hydroxide, aluminum hydroxide, calcium hydroxide, chromium hydroxide, and others.

Metal silicate includes zinc silicate and aluminum silicate, among others, and metal carbonate includes zinc carbonate, aluminum carbonate, copper carbonate, etc.

Inorganic porous fine particles are porous fine particles made from an inorganic material, and, for example, inorganic porous matter of calcium silicate may be used, and its manufacturing method may be varied freely, and in particular when obtained by surface activation method, the particle shape is spherical and is preferable from the viewpoint of dispersion and skin touch, but it is not particularly limited. An example of inorganic porous fine particles manufactured by surface activation method is disclosed in Japanese Patent Publication No. 57-55454 as spherical inorganic porous fine particles obtained by surface reaction method.

In the invention, particularly preferred inorganic porous fine particles is silicic anhydride porous fine particles. They are spherical, being made of silicic anhydride, and manufactured by surface reaction method, or wet process by silicic sol formation.

Figure 2:
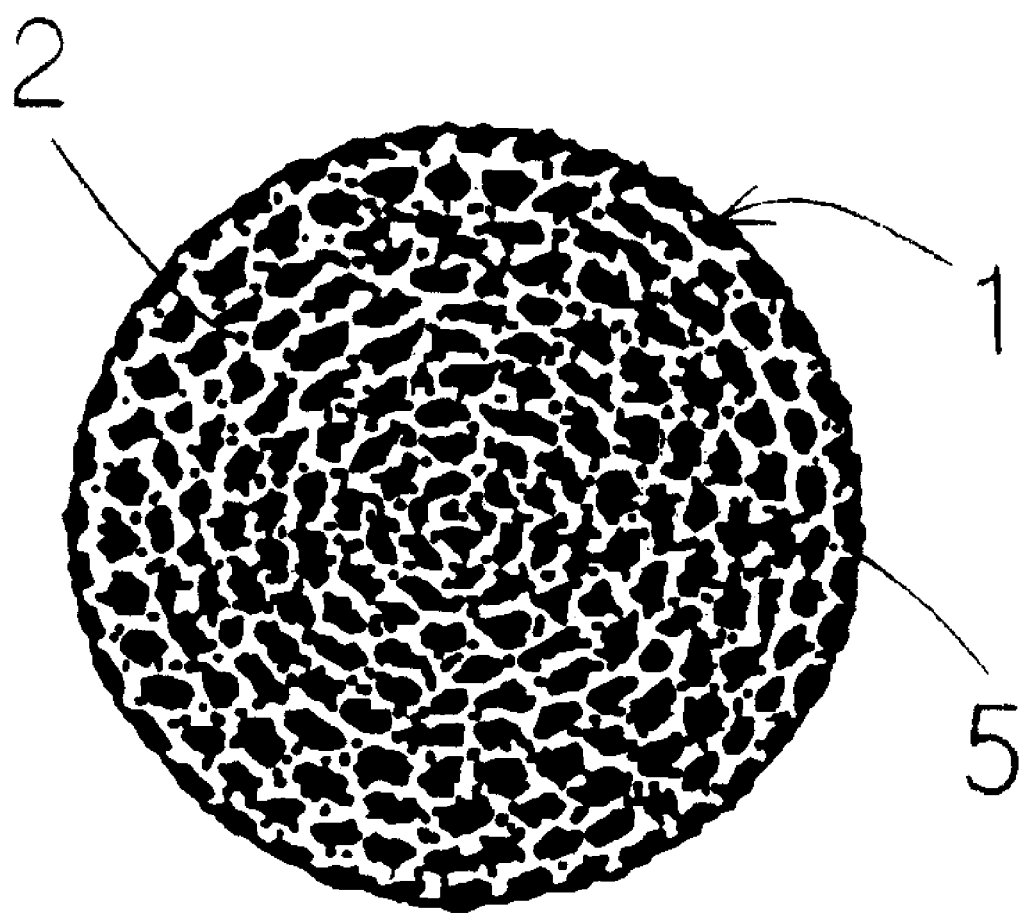
FIG. 2 is a sectional view showing an example of non-hollow inorganic porous fine particles impregnating a chemical of the invention.

In this surface reaction method, a waterdrop-in-oil type emulsion of organic solvent and surface active agent is prepared in an aqueous solution of an inorganic compound, and it is mixed with other aqueous solution to cause sedimentation reaction on the waterdrop interface, and by removing byproducts and surface active agent after forming an inorganic shell, hollow inorganic porous fine particles or non-hollow (that is, not having hollow space) inorganic porous fine particles are obtained. One of commercial products is Godball, a tradename of inorganic porous fine particles of Suzuki Yushi Kogyo KK In the wet process by silicic sol formation, silicic soda and sulfuric acid are mixed, and silicic sol is prepared, and it is gradually polymerized and gelated, and colloidal particles are pulverized in micron size. One of commercial products is Silicia, a tradename of non-hollow porous fine particles of Fuji Silicia Chemical KK The inorganic porous fine particles to be used in the invention are, in both hollow and non-hollow types, required to have the following features. That is, the particle size should be 0.5 to 50 microns, more preferably 0.5 to 26 microns. The surface pore diameter is 20 to 150 angstroms. The specific surface area is 20 to 800 $m^2/g$, preferably 300 to 700 $m^2/g$. The pore volume is 0.01 to 1.50 ml/g, and the bulk density is 0.18 to 0.40 $g/cm^3$. In the hollow inorganic porous fine particles, a liquid chemical or a chemical dissolved or dispersed in a solvent can be incorporated by 160 to 180 ml/100 g, and in non-hollow inorganic porous fine particles, a chemical dissolved or dispersed in a solvent can be contained by 80 to 175 ml/100 g. A schematic sectional structure of inorganic porous fine particles carrying the chemical is shown in FIG. 1. In the illustrated example, the chemical 2 is contained in a capsule form in hollow inorganic porous fine particles 1 of which wall substance is silicic anhydride, and the chemical exudes gradually from innumerable pores 3 existing in the wall surface, and the drug effect lasts for a long period. Or, as shown in FIG. 2, the chemical 2 may be also impregnated in gaps 5 of the non-hollow inorganic porous fine particles 1.

Of the inorganic porous fine particles manufactured in the surface activation method by Suzuki Yushi Kogyo KK (tradename: Godball), physical properties of non-hollow porous spherical particles are shown in Table 1. As an example of manufacture by wet process by silicic sol formation, physical properties of non-hollow porous fine particles by Fuji Silicia Chemical KK (tradename: Silicia) are shown in Table 2. Physical properties of hollow porous spherical particles of inorganic porous fine particles of Suzuki Yushi Kogyo KK (tradename: Godball) are shown in Table 3.

TABLE 1

Physical properties of non-hollow porous spherical particles

| | Product number of Godball | | | | | |
|---|---|---|---|---|---|---|
| | E-2C | E-6C | D-11C | E-16C | E-6CK | PF-6CB |
| Particle size range ($\mu$m) | 0.5~3.0 | 0.5~6.0 | 0.5~11.0 | 0.5~18.0 | 0.9~7.5 | 2~15 |
| Mean particle size ($\mu$m) | 0.9~1.4 | 2.0~2.5 | 3.3~3.6 | 4.0~5.3 | 2.5 | 5.3 |
| True density (g/cm$^3$) | 2.10 | 2.10 | 2.10 | 2.10 | 2.10 | |
| Bulk density (g/cm$^3$) | 0.18~0.25 | 0.22~0.25 | 0.29~0.40 | 0.30~0.35 | 0.21 | |
| Surface pore daimeter range (Å) | 50~150 | 50~150 | 20~60 | 50~150 | 50~150 | 449.0 |
| Specific surface area (m$^2$/g) | 350~500 | 600~700 | 450~550 | 300~550 | 260 | 214.7 |
| Pore volume (ml/g) | 1.30~1.40 | 1.20~1.30 | 0.50~0.60 | 1.00~1.20 | 0.644 | 1.345 |
| Oil feed volume (ml/100 g) | 160~175 | 130~140 | 80~90 | 105~130 | 133.0 | 307 |

TABLE 2

Physical properties of non-hollow porous spherical particles

| | Grade of Silicia | | | | |
|---|---|---|---|---|---|
| | 730 | 740 | 550 | 530 | 250 |
| Particle size range ($\mu$m) | 1.7~10.4 | 1.7~12.5 | 1.7~10.4 | 1.2~6.0 | 2.4~12.5 |
| Mean particle size ($\mu$m) | 3.0 | 3.5 | 2.7 | 1.9 | 2.7 |
| Specific surface | 700 | 700 | 500 | 500 | 300 |

TABLE 2-continued

Physical properties of non-hollow porous spherical particles

| | Grade of Silicia | | | | |
|---|---|---|---|---|---|
| | 730 | 740 | 550 | 530 | 250 |
| area (m²/g) | | | | | |
| Oil feed volume (ml/100 g) | 95 | 95 | 160 | 170 | 310 |

TABLE 3

Physical properties of hollow porous spherical particles

| | Product number of Godball | |
|---|---|---|
| | B-6C | B-25C |
| Particle size range (μm) | 0.5~6.0 | 0.5~25.0 |
| Mean particle size (μm) | 2.0~2.5 | 12.0~14.0 |
| True density (g/cm³) | 2.10 | 2.10 |
| Bulk density (g/cm³) | 0.18~0.20 | 0.22~0.44 |
| Surface pore daimeter range (Å) | 50~150 | 50~150 |
| Specific surface area (m²/g) | 550~600 | 650~700 |
| Pore volume (ml/g) | 1.20~1.30 | 1.20~1.30 |
| Oil feed volume (ml/100 g) | 160~170 | 170~180 |

In the inorganic porous fine particles carrying the chemical, the active ingredient of the chemical is impregnated in the pore volume of the inorganic porous fine particles, and the pore volume of the inorganic porous fine particles is filled with the chemical by vacuum method or direct absorption method.

The carrying amount of the chemical in the inorganic porous fine particles is preferably about 1 to 500 wt. %, and more preferably 10 to 130 wt. %. That is, if less than 1 wt. %, the drug effect duration is short, and if more than 500 wt. %, it is excessive and flows out from the inorganic porous fine particles, and hence the specified range is preferred.

The inorganic porous fine particles carrying the chemical can be contained in the internal liquid composition by 0.01 to 60 wt. %, preferably 1 to 30 wt. %. That is, if less than 0.01 wt. %, the drug effect duration is short, and if more than 60 wt. %, the flowability of the disperse solution is lost, and dispersion is disabled, and hence the specified range is preferred. Incidentally, of all inorganic porous fine particles blended in the internal solution composition, it is desired that 40 to 90% of inorganic porous fine particles may have a surface pore diameter of 50 to 150 angstroms.

The disperse solution of the invention is a liquid for dispersing the inorganic porous fine particles carrying the chemical, and it is preferred to be in a liquid state in the environments of 0 to 50 deg. C, and, depending on the application, water or organic solvent, or mixture may be used. As the organic solvent, alcohols, ethers, ketones, and aldehydes may be preferably used among others. Specific examples include methyl alcohol, ethyl alcohol, propyl alcohol, isopropyl alcohol, butyl alcohol, and others. Ethers include petroleum ether, diethyl ether, etc. Ketones include acetone, methyl ethyl ketone, etc. Aldehydes include formaldehyde, acetaldehyde, etc. Preferably, alcohols should be used, and more preferably, methyl alcohol, ethyl alcohol, propyl alcohol, or isopropyl alcohol with 1 to 3 carbon atoms should be used.

As a particularly preferred mode of use of the disperse solution is to use a mixture of alcohol and water because this is used in the living space of people, and the content of alcohol is preferred to be 75 to 95 wt. %, so that the chemical may be dispersed more uniformly.

The above conditions are common to the first, second and third internal liquid compositions of the invention. Blending substances used in the first internal liquid composition of the invention are described below. That is, the first internal liquid composition of the invention comprises inorganic porous fine particles carrying the chemical, disperse solution, acrylic acid polymer, and alkali, end the acrylic acid polymer and alkali are sequentially described below.

The acrylic acid polymer is also known as polyacrylic acid, and is prepared by polymerizing two or more acrylic acids, and in particular the crosslinking type acrylic acid polymer can be used.

Specific examples of the acrylic acid polymer include Junlon PW-110 and Junlon PW-150 of Nippon Junyaku KK, Carbopole 907, Carbopole 910, Carbopole 934, Carbopole 940 and Carbopole 941 of Showa Denko KK, Aspec HV-505 of Seitetsu Kagaku Kogyo KK, and Hibiswako 103, Hibiswako 104, Hibiswako 105, Hibiswako 204 and Hibiswako 304 of Wako Junyaku KK, among others. The content of the acrylic acid polymer in the internal liquid composition is 0.0001 to 6 wt. %, preferably 0.01 to 0.5 wt. %. That is, if less than 0.0001 wt. %, the viscosity is too low to disperse uniformly, or if more than 6 wt. %, the viscosity is too high to disperse uniformly, and therefore it is desired to define within the specified range.

The alkali is a water-insoluble or hardly water-insoluble matter for thickening the disperse solution by neutralizing the acrylic acid polymer. Specific examples of alkali include polyoxyethylene oleyl amine, polyoxyethylene stearyl amine, polyoxyethylene propylene amine, polyoxyethylene propylene diamine, polyoxyethylene tallow amine, polyoxyethylene palm amine, dibutyl amine, tri-(2-ethyl) hexyl amine, tributyl amine, N,N-dibutyl-2-ethyl hexyl amine, diisobutyl amine, diallyl amine, di-sec-isobutyl amine, tri-allyl amine, N,N-dimethyl butyl amine, N,N-dimethyl allyl amine, 1,2-dimethyl propyl amine, N-methyl diallyl amine, N-ethyl-1,2-dimethyl propyl amine, N,N-diisopropyl ethyl amine, hexyl amine, dibenzyl amine, N-methyl hexyl amine, dimethyl benzyl amine, di-n-octyl amine, 2-ethyl hexyloxy propyl amine, tri-n-octylamine, dibutyl aminopropyl amine, N-methyl-di-n-octyl amine, 2-ethyl hexyl amine, di-(2-ethyl) hexyl amine, and others. The content of the alkali is the amount necessary for neutralizing the acrylic acid polymer, and, depending on the content of the acrylic acid polymer, it is 0.00001 to 20 wt. %, preferably 0.01 to 0.5 wt. %. That is, if less than 0.00001 wt. %, the neutralization is insufficient, and dispersion is not uniform, or if more than 20 wt. %, it is excessive, and hence it is desired to define within the specified range.

The first internal liquid composition of the invention may comprise surface active agent, moisturizing or others in addition to the above substances. In particular, the surface active agent is advantageous for enhancing the dispersion performance of the inorganic porous fine particles.

Usable examples of surface active agent include anionic surface agent, cationic surface active agent, amphoteric surface active agent, and nonionic surface active agent, and since it is particularly used in human subjects, those listed in the Japanese Standards of Cosmetic Ingredients are preferred. In the surface active agent, the HLB value is preferred to be 1 to 20, more preferably 5 to 15. By using in the HLB range of 5 to 15, the chemical and inorganic porous fine particles can be dispersed more uniformly. The content of the surface active agent in the internal liquid composition is preferred to be 0.01 to 5 wt. %.

That is, if less than 0.01 wt. %, it is hard to disperse, and if more than 5wt. %, the surface active agent is excessively, and hence it is desired to define within the specified range.

Specific examples of surface active-agent include the following.

Anionic surface active agents include zinc laurate, zinc myristate, magnesium myristate, zinc palmitate, magnesium stearate, zinc stearate, aluminum stearate, calcium stearate, sodium lauryl sulfate, lauric acid triethanol amine, sodium cetyl sulfate, polyoxy ethylene lauryl ether sulfuric triethanol amine, sodiumpolyoxy ethylene lauryl ether sulfate, polyoxy ethylene lauryl ether phosphate, sodium polyoxy ethylene lauryl ether phosphate, polyoxy ethylene cetyl ether phosphate, sodium polyoxy ethylene cetyl ether phosphate, polyoxy ethylene stearyl ether phosphate, polyoxy ethylene oleyl ether phosphate, sodium polyoxy ethylene oleyl ether phosphate, polyoxy ethylene alkyl phenyl ether phosphate, polyoxy ethylene alkyl phenyl ether phosphoric triethanol amine, sodium polyoxy ethylene alkyl phenyl ether phosphate, lauroyl sarcocin sodium, soybean phospholipid, and others.

Cationic surface active agents include ammonium stearyl trimethyl chloride, ammonium distearyl dimethyl chloride, benzalkonium chloride, benzethonium chloride, ammonium stearyl dimethyl benzyl chloride, cetyl pyridinium chloride, alkyl isoqunolinium bromide, domiphen bromide, and others.

Amphoteric surface active agents include sodium beta-lauryl aminopropionate, betaine lauryl dimethyl aminoacetic acid, 2-alkyl-N-carboxymethyl-N-hydroxy ethyl imidazolinium betaine, and others.

Nonionic surface active agents include self-emulsion type glycerin monostearate, oleophilic glycerin monostearate, oleophilic glyceride monoleate, ethylene glycol monostearate, propylene glycol monostearate, propylene glycol dioleate, sorbitan monolaurate, sorbitan monopalmitate, sorbitan monostearate, sorbitan monoleate, sorbitan sesquioleate, sorbitan trioleate, sucrose fatty acid ester, monoethanol amide undecylate, diethanol amide laurate, palm oil fatty acid diethanol amide, polyethylene glycol monolaurate, polyethylene glycol monostearate, polyethylene glycol monoleate, myristyl lactate, cetyl lactate, polyoxy ethylene lauryl ether, polyoxy ethylene cetyl ether, polyoxy ethylene stearyl ether, polyoxy ethylene oleyl ether, polyoxy ethylene octyl phenyl ether, polyoxy ethylene nonyl phenyl ether, polyoxy ethylene stearic amide, polyoxy ethylene glycerin monostearate, polyoxy ethylene sorbit monolaurate, polyoxy ethylene sorbitan monolaurate, polyoxy ethylene sorbitan monopalmitate, polyoxy ethylene sorbitan monostearate, polyoxy ethylene monostearate, polyoxy ethylene sorbitan hexastearate, polyoxy ethylene sorbitan monoleate, polyoxy ethylene sorbitan trioleate, polyoxy ethylene sorbit tetraoleate, polyoxy ethylene sorbit beeswax, polyoxy ethylene castor oil, polyoxy ethylene hardened castor oil, polyoxy ethylene lanolin, and others.

As other compounds, in particular, warmth keeping compounds may be mixed for adjusting the evaporation performance. The warmth keeping compounds include glycerin, oil and fat. The mixing content is 0.01 to 50 wt. %, preferably 1 to 10 wt. %.

One of the methods of manufacturing the first internal liquid composition of the invention is a method of adding acrylic polymer and alkali to the disperse solution for thickening, and adding further the inorganic porous fine particles carrying the chemical and the surface active agent for dispersing.

In execution of this manufacturing method, it is preferred to perform at room temperature of 10 to 35 deg. C, in particular, and the acrylic acid polymer is added while stirring to disperse uniformly. By neutralizing the disperse solution by adding the alkali, the disperse solution becomes viscous. As measured by type B viscometer, for example, the value of the viscosity should be adjusted to 10 to 300000 cps, preferably 400 to 1000 cps. That is, this range is preferred because it is hard to disperse uniformly when the viscosity is out of this range.

In this disperse solution heightened in viscosity, the inorganic porous fine particles carrying the chemical, and other additive compounds as required such as surface active agent are added, and stirred and dispersed uniformly, and the first internal liquid composition of the invention is obtained. As the means of dispersing uniformly, using a homogenizer, it is preferred to homogenize by stirring at rotating speed of 10 to 13000 rpm, preferably at high speed of 5000 to 8000 rpm. That is, if less than 10 rpm, the chemical cannot be dispersed uniformly, or if the rotating speed is more than 13000 rpm, the acrylic acid polymer is sheared, and the chemical cannot be dispersed, and hence it is desired to define within the specified range.

Blending substances used in the second internal liquid composition of the invention are described below. That is, the second internal liquid composition of the invention comprises synthetic resin fine particles, in addition to the inorganic porous fine particles carrying the chemical and the disperse solution. The inorganic porous fine particles carrying the chemical and the disperse solution may be substantially same as in the first internal liquid composition, and mainly synthetic resin fine particles are described below.

Herein, synthetic resin fine particles are spherical particles of synthetic resin, such as polyethylene, tetrafluoroethylene, nylon, polymethyl methacrylate, polystyrene, polyacetal, polypropylene, ethylene-acrylic acid copolymer, etc. The distribution of diameter of synthetic resin fine particles is preferred to be nearly same as the distribution of diameter of silicic anhydride porous fine particles. That is, the diameter of synthetic resin fine particles is 0.1 to 50 microns, preferably 2 to 20 microns, more preferably 2 to 15 microns. The mean particle size of synthetic resin fine particles is preferred to be larger than the mean particle size of silicic anhydride porous fine particles.

Synthetic resin fine particles are preferred to be same as silicic anhydride electrically in the electric charge, contradictory in the charge characteristic to each other, easy to depart from each other in shape, and not contacting physically. Meanwhile, since the synthetic resin particles are soft and elastic, they compensate for the hardness of the silicic anhydride porous fine particles. That is, when this compound is used on the surface of the human body, both dry feel and smooth feel are exhibited at the same time.

The content of the synthetic resin fine particles in the internal liquid composition may be varied appropriately, but is preferred to be 0.01 to 30 wt. %, and the content of the inorganic porous fine particles in the internal liquid composition is preferred to be 0.01 to 60 wt. % as mentioned above.

The blending ratio of the silicic anhydride porous fine particles and synthetic resin fine particles may be varied depending on the kind and particle size of the silicic anhydride porous fine particles and synthetic resin fine particles, blending content in the internal liquid composition, and other conditions. That is, the silicic anhydride porous fine particles and synthetic resin fine particles may be blended in the range of the specified contents, and most preferably synthetic resin fine particles should be blended by 0.1 to 20 parts by weight in 1 part by weight of the silicic anhydride porous fine particles.

In this second internal liquid composition, in addition to the above blending, it is also possible to blend other substances, for example, the thickening agent, wetting agent, and surface active agent and moisturizer as mentioned in the first internal liquid composition.

Blending substances used in the third internal liquid composition of the invention are described below. That is, the third internal liquid composition of the invention comprises acrylic acid polymer, alkali, surface active agent and synthetic resin fine particles, in addition to the inorganic porous fine particles carrying the chemical and the disperse solution. The acrylic acid polymer, alkali and surface active agent are same as used in the first internal liquid composition, and the synthetic resin fine particles are same as in the second internal liquid composition, and are not particularly described below. Same as in the first and second a-internal liquid compositions, too, other substances than the blending substances shown as the third internal liquid composition of the invention may be also used.

The invention is hereinafter described while referring to the embodiments, but it must be noted that the invention is not limited to these examples alone.

First, as the first internal liquid composition of the invention, three embodiments (embodiments 1 to 3), and three corresponding comparative examples (comparative examples 1 to 3) are shown in Table 4.

<Embodiment 1>

In embodiment 1, using N,N-diethyl-m-toluamide (DEET) of Mitsubishi Gas Chemical KK having a mosquito repelling effect as the chemical, the internal liquid composition was prepared by blending as shown in Table 4. More specifically, in the ethyl alcohol used as disperse solution, an acrylic acid polymer was added and mixed to give viscosity, and to further increase viscosity and to adjust the pH, POE palm amine as alkali, that is, polyoxy ethylene palm amine (tradename: Emison-45, Lion KK) was added. Further, water and glycerin as moisturizer were added, and a mixed liquid was prepared. Inorganic porous fine particles of silica preliminarily carrying the DEET were added to the mixed liquid, and homogenized for 5 minutes by a homogenizer at room temperature at rotating speed of 6000 rpm, and an internal liquid composition was prepared.

As the inorganic porous fine particles, inorganic silicic porous fine particles of Suzuki Yushi Kogyo KK, Godball E-6CK, were used. The same product was used in embodiments 2 and 3, and comparative example 1.

<Embodiment 2>

In embodiment 2, an internal liquid composition was prepared by the same operation as in embodiment 1. What differs from embodiment 1 is that polyoxy ethylene lauryl ether (shown as POE lauryl ether in Table 4) was blended as surface active agent together with water and glycerin.

<Embodiment 3>

In embodiment 3, an internal liquid composition was prepared by the same operation as in embodiment 1. What differs from embodiment 1 is that eucalyptus oil, one of natural perfumes, was used as the chemical.

<Comparative example 1>

Comparative example 1 differs from the foregoing embodiments in that acrylic acid polymer and alkali were not used. That is, ethyl alcohol, water, and glycerin were added, and a mixed liquid was prepared. Inorganic porous fine particles preliminarily carrying the DEET were added to the mixed liquid, and an internal liquid composition was prepared by homogenizing by a homogenizer at room temperature, for 5 minutes, at rotating speed of 6000 rpm.

<Comparative example 2>

Comparative example 2 differs from the foregoing embodiments in that inorganic porous fine particles were not used. That is, acrylic acid polymer was added to ethyl alcohol and mixed, and POE palm amine was further added to give viscosity. To this mixture, glycerin, water, and polyoxy ethylene lauryl ether (nonionic surface active agent) was added and mixed, and a mixed liquid was prepared. Different from the foregoing embodiments, without using inorganic porous fine particles, DEET was directly mixed in the mixed solution, and an internal liquid composition was prepared by homogenizing by a homogenizer at room temperature, for 5 minutes, at rotating speed of 6000 rpm.

<Comparative example 3>

In comparative example 3, an internal liquid composition was prepared in the same operation as in comparative example 2. However, instead of DEET, the same perfume as in embodiment 3 was used.

TABLE 4

|  |  | First Invention | | | | | |
|---|---|---|---|---|---|---|---|
|  |  | Embodiment 1 | Embodiment 2 | Embodiment 3 | Comparative example 1 | Comparative example 2 | Comparative example 3 |
| Inorganic porous fine particles | Godball | 3.5 (w. %) | 3.0 | 3.0 | 3.5 | — | — |
| Acrylic acid polymer |  | 0.1 | 0.1 | 0.1 | — | 0.1 | 0.1 |
| Alkali | POE palm amine | 0.3 | 0.3 | 0.3 | — | 0.3 | 0.3 |
| Active ingredient | DEET | 7.0 | 7.0 |  | 7.0 | 7.0 |  |
|  | Eucalyptus oil |  |  | 7.0 |  |  | 7.0 |
|  | Glycerine | 3.0 | 3.0 | 3.0 | 3.0 | 3.0 | 3.0 |
|  | POE lauryl ether |  | 0.5 | 0.5 |  |  |  |
| Disperse solution | Purified water | 5.0 | 5.0 | 5.0 | 5.0 | 5.0 | 5.0 |
|  | Ethyl alcohol | 81.1 | 81.1 | 81.1 | 81.5 | 84.6 | 84.6 |
| Propellant |  | LPG | Carbon dioxide | Carbon dioxide | LPG | Carbon dioxide | Carbon dioxide |

TABLE 4-continued

|  |  | First Invention | | | | | |
|---|---|---|---|---|---|---|---|
|  |  | Embodiment 1 | Embodiment 2 | Embodiment 3 | Comparative example 1 | Comparative example 2 | Comparative example 3 |
| Evaluation | | | | | | | |
| Internal liquid | Particle sediment | ◎ | ◎ | ◎ | X | — | — |
|  | Particle re-dispersion | ◎ | ◎ | ◎ | X | — | — |
| Product | Particle sediment | ◎ | ○ | ○ | X | — | — |
|  | Particle re-dispersion | ◎ | ○ | ○ | X | — | — |
|  | Prolonged action of effect | ○ | ○ | ○ | ○ | X | X |
|  | Dry & smooth feel | ○ | ○ | ○ | ○ | X | X |
| Overall effect | | ○ | ○ | ○ | X | X | X | following tests were conducted on the embodiments and comparative examples, and test methods are described below, and results are shown in Table 4.

<Testing method of dispersion performance of internal liquid>

After stirring sufficiently, 50 ml of internal solution is transferred into a glass bottle, and let stand still.

Observing the state of the internal liquid after letting stand still, the state (the time) of the white-particle layer sediment on the bottle bottom is observed. Generally, the slower the sedimentation, the better is considered to be the dispersion of particles in the internal liquid. Herein, the evaluation is poor (X) if the time required from the still state of the internal liquid until sedimentation of white particle layer is within 10 seconds, the evaluation is fair (Δ) from 10 seconds to 30 seconds, and the evaluation is good (○) if more than 30 seconds.

<Test result of dispersion performance of internal liquid>

Embodiments 1 to 3 and comparative example 1 were tested according to the above testing method of internal liquid. Results are shown in Table 4, in which embodiments 1 to 3 presented excellent dispersion as compared with comparative example 1.

<Testing method of re-dispersion performance of internal liquid>

After stirring sufficiently, 50 ml of internal solution is transferred into a glass bottle, and let stand still for 1 week, and then the bottle is inverted upside down slowly. Observing the motion of white particles settling in the bottle bottom, it is checked if the particles are dispersed in the entire bottle or not. If not dispersing, the bottle is raised upright again, and the dispersion is observed once more. In this way, until the particles are dispersed uniformly in the entire bottle, inverting and raising of bottle are repeated, and the number of times is counted. After inverting 11 times or more, if particles are left over in the bottle bottom, the evaluation is poor (X), when particles are dispersed in the entire bottle by 5 to 10 times of inverting, the evaluation is fair (Δ), when particles are dispersed in the entire bottle by 3 or 4 times of inverting, the evaluation is good (○), and when particles are dispersed in the entire bottle by 1 or 2 times of inverting, the evaluation is excellent (◎).

<Test result of dispersion performance of internal liquid>

Embodiments 1 to 3 and comparative example 1 were tested according to the above testing method of internal liquid. Results are shown in Table 4, in which embodiments 1 to 3 presented excellent dispersion as compared with comparative example 1.

<Testing method of dispersion performance of product>

To evaluate dispersion and re-dispersion of product, products for observation were prepared in the same condition as in manufacture of aerosol products above. The internal liquid obtained in the embodiments and comparative examples above was put in a pressure-proof glass bottle by 50 ml each, a valve was attached, and a propellant was charged. In embodiment 1 and comparative example 1, liquid petroleum gas (LPG) was used as propellant to fill to an internal pressure of 4 kg/cm$^2$. In embodiments 2 and 3, carbon dioxide was used as propellant to fill to an internal pressure was 5.5 kg/cm$^2$.

After sufficiently stirring each pressure-proof glass bottle, it is let stand still. Observing the state of the internal liquid after letting stand still, the state (the time) of the white particle layer sediment on the bottle bottom is observed. Generally, the slower the sedimentation, the better is considered to be the dispersion of particles in the internal liquid. Herein, the evaluation is poor (X) if the time required from the still state of the internal liquid until sedimentation of white particle layer is within 10 seconds, the evaluation is fair (Δ) from 10 seconds to 30 seconds, and the evaluation is good (○) if more than 30 seconds.

<Test result of dispersion performance of product>

Embodiments 1 to 3 and comparative example 1 were tested according to the above testing method of internal liquid. Results are shown in Table 4, in which embodiments 1 to 3 presented excellent dispersion as compared with comparative example 1.

<Testing method of re-dispersion performance of product>

In the testing method of re-dispersion of product, the pressure-proof glass bottle prepared in the same condition as in the test of dispersion of product is let stand still for 1 week, and then the bottle is inverted upside down slowly. Observing the motion of white particles settling in the bottle bottom, it is checked if the particles are dispersed in the entire bottle or not. If not dispersing, the bottle is raised upright again, and the dispersion is observed once more. In this way, until the particles are dispersed uniformly in the entire bottle, inverting and raising of bottle are repeated, and the number of times is counted. After inverting 11 times or more, if particles are left over in the bottle bottom, the evaluation is poor (X), when particles are dispersed in the entire bottle by 5 to 10 times of inverting, the evaluation is fair (Δ), when particles are dispersed in the entire bottle by 3 or 4 times of inverting, the evaluation is good (○), and when particles are dispersed in the entire bottle by 1 or 2 times of inverting, the evaluation is excellent (◎).

<Test result of dispersion performance of product>

Embodiments 1 to 3 and comparative example 1 were tested according to the above testing method of internal liquid. Results are shown in Table 4, in which embodiments 1 to 3 presented excellent dispersion as compared with comparative example 1.

<Testing method 1 of prolonged action of effect (efficacy) of product (repellent)>

The duration of effect (efficacy) was tested in products of embodiments and comparative examples using the DEET as a kind of repellent as the chemical. In this method, an assay filter paper (tradename: No. 3, manufactured by Advantech Toyo KK) of 110 mm in diameter is placed at a distance of 100 mm from the end of the aerosol valve of the aerosol product filled with the products of the embodiments and comparative examples. Injecting the internal liquid from the aerosol valve, about 5 g is applied on this filter paper, and adsorbed. Further, the filter paper is placed in a thermostatic oven controlled at 25 deg. C, and the sustained-release test is effected. On the other hand, preparing a rearing case of 30×30×30 cm, divided in two chambers so as to communicate with each other, the repellent effect on common gnats was investigated. In this method of investigation, the filter paper used in sustained-release test was put in one chamber, and 20 mosquitoes were put in this filter paper placed chamber, and the number of insects moving to the other chamber without filter paper was observed every day, and the results are shown in Table 4.

When the number of insects moving to the other chamber 1 day later was 4 or less, the evaluation was poor (X).

When the number of insects moving to the other chamber 2 or 9 days later was 15 or more, the evaluation was fair (Δ).

When the number of insects moving to the other chamber 10 days later was 15 or more, the evaluation was good (○).

When all insects moved to the other chamber 10 days later, the evaluation was excellent (◎).

<Test result of prolonged action of effect (efficacy) of product (repellent)>

According to the testing method of prolonged action of effect (efficacy) of the product, embodiments 1 and 2 and comparative examples 1 and 2 were tested. Results are shown in Table 4, in which embodiments 1 and 2 presented better prolonged action of effect (efficacy) as compared with comparative examples 1 and 2.

<Testing method 2 of prolonged action of effect (efficacy) of product (perfume)>

In products of embodiments and comparative examples using eucalyptus oil as the chemical, about 5 g was injected from a distance of 100 mm from the end of the aerosol valve to an assay filter paper (tradename: No. 3, manufactured by Advantech Toyo KK) of 110 mm in diameter, and applied and adsorbed, and the filter paper is placed in a thermostatic oven controlled at 25 deg. C, and the sustained-release test is effected. The aroma effect was evaluated by human smelling sense, and results are shown in Table 4.

When the aroma was lost in 1 to 4 days, the evaluation was poor (X).

When the aroma was lost in 5 to 9 days, the evaluation was fair (Δ).

When the aroma remained in 10 days, the evaluation was good (○).

When a strong aroma remained in 10 days, the evaluation was excellent (◎).

<Test result of prolonged action of effect (efficacy) of product (perfume)>

According to the testing method of prolonged action of effect (efficacy) of the product, embodiment 3 and comparative example 3 were tested. Results are shown in Table 4, in which embodiment 3 presented better prolonged action of effect (efficacy) as compared with comparative example 3.

<Testing method of touch of product>

In products of embodiments and comparative examples, the internal content is injected to the human skin, and the skin touch is investigated 5 minutes later. The evaluation is poor (X) when a stickiness is felt, the evaluation is fair (Δ) when a slight stickiness is felt, the evaluation is good (○) when a dry and smooth feeling is obtained, and the evaluation is excellent (◎) when an extreme dry and smooth feeling is obtained.

<Test result of touch of product>

According to the testing method of touch of product, embodiments 1 to 3 and comparative examples 1 to 3 were tested. Results are shown in Table 4, in which embodiments 1 to 3 presented a better touch than comparative examples 2 and 3.

As the second internal liquid composition of the invention, six embodiments (embodiments 4 to 9) and corresponding two comparative examples (comparative examples 4, 5) are shown below.

<Embodiments 4 to 9>

In embodiments 4 to 9 and comparative examples 4 and 5, too, the internal liquid composition was prepared by blending as shown in Table 5, by using N,N-diethyl-m-toluamide (DEET) having a mosquito repellent effect as the chemical. In embodiment 9, aluminum hydroxy chloride having an antiperspirant effect was blended as the chemical. These chemicals were blended by carrying on silicic anhydride porous fine particles. The silicic anhydride porous fine particles were Godball E-6C of Suzuki Yushi Kogyo KK in embodiments 4, 6 to 9 and comparative examples 4 and 5, and Silicia 530 of Fuji Silicia Chemical KK in embodiment 5. In embodiments 4 to 9, polyethylene powder (Flow Peas CL-2080 of Sumitomo Seika KK) was blended as synthetic resin particles, while synthetic resin particles were not blended in comparative examples 4 and 5.

As other components, in embodiment 4, concentrated glycerin and 99% denatured ethyl alcohol were blended.

In embodiment 5, 1,3-butylene glycol, sodium POE oleyl ether phosphate (Phosphanol RO-720N of Toho Kagaku Kogyo KK), and 99% denatured ethyl alcohol were blended.

In embodiment 6, 1,3-butylene glycol and 99% denatured ethyl alcohol were blended.

In embodiment 7, concentrated glycerin, sodium POE oleyl ether phosphate (Phosphanol RO-720N of Toho Kagaku Kogyo KK), and 99% denatured ethyl alcohol were blended.

In embodiment 8, concentrated glycerin, sodium POE oleyl ether phosphate (Phosphanol RO-720N of Toho Kagaku Kogyo KK), and purified water were blended.

In embodiment 9, aluminum hydroxy chloride, IPM, and purified water were blended.

In comparative example 4, concentrated glycerin, sodium POE oleyl ether phosphate (Phosphanol RO-720N of Toho Kagaku Kogyo KK), purified water, and 99% denatured ethyl alcohol were blended, and also carboxy vinyl polymer (Carbopole 941, Nikko Chemicals) was blended as the viscosity regulating agent.

In comparative example 5, concentrated glycerin and 99% denatured ethyl alcohol were blended.

TABLE 5

|  |  | Second Invention | | | | | | Comparative example 4 | Comparative example 5 |
|---|---|---|---|---|---|---|---|---|---|
|  |  | Embodiment 4 | Embodiment 5 | Embodiment 6 | Embodiment 7 | Embodiment 8 | Embodiment 9 | | |
| Inorganic porous fine particles | Godball | 3.5 (w. %) | | 2.5 | 3.0 | 3.0 | 3.0 | 3.0 | 3.0 |
|  | Silicia | | 2.5 | | | | | | |
| Synthetic resin fine particles (Polyethylene powder) | | 1.0 | 0.8 | 0.8 | 0.6 | 1.0 | 0.6 | | |
| Viscosity regulating agent (Carboxy vinyl polymer) | | | | | | | | 1.8 | |
| Active ingredient | DEET | 7.0 | 7.0 | 7.0 | 9.0 | 7.0 | | 7.0 | 7.0 |
|  | Aluminum hydroxy chloride | | | | | | 6.0 | | |
|  | Glycerin | 3.0 | | | 3.0 | 3.0 | | 5.0 | 3.0 |
|  | 1,3-butylene glycol | | 2.5 | 2.5 | | | | | |
|  | IPM | | | | | | 2.0 | | |
|  | Sodium POE oleyl ether phosphate | | 1.1 | | 2.0 | 2.0 | | 1.1 | |
| Disperse solution | Purified water | | | | | 84.0 | 15.0 | 5.0 | |
|  | Ethyl alcohol | 86.0 | 86.1 | 87.2 | 82.4 | | 73.4 | 77.1 | 87.0 |
| Propellant | | LPG | Carbon dioxide | Carbon dioxide | LPG | Nitrogen gas | Carbon dioxide | Carbon dioxide | Carbon dioxide |
| Evaluation | | | | | | | | | |
| Internal liquid | Particle sediment | ⊚ | ⊚ | ⊚ | ⊚ | ⊚ | ⊚ | ⊚ | X |
|  | Particle re-dispersion | ⊚ | ⊚ | ⊚ | ⊚ | ⊚ | ⊚ | ⊚ | X |
| Product | Particle sediment | ⊚ | ⊚ | ⊚ | ⊚ | ⊚ | ⊚ | X | X |
|  | Particle re-dispersion | ⊚ | ⊚ | ⊚ | ⊚ | ⊚ | ⊚ | X | X |
|  | Prolonged action of effect | ○ | ○ | ○ | ○ | ○ | / | ○ | ○ |
|  | Dry & smooth feel | ⊚ | ⊚ | ⊚ | ⊚ | ○ | ○ | ○ | Δ |
| Overall effect | | ○ | ○ | ○ | ○ | ○ | ○ | X | X |

<Testing method of dispersion and re-dispersion of internal liquid>

Dispersion and re-dispersion of internal liquid were tested in the same method as described above.

<Test result of dispersion and re-dispersion of internal liquid>

Test results of dispersion and re-dispersion of internal liquid are shown in Table 5, in which embodiments 4 to 9 presented better dispersion and re-dispersion as compared with comparative example 5.

<Testing method of dispersion and re-dispersion of product>

Dispersion and re-dispersion of product were tested in the same method as described above.

In embodiments 4, 5, 9 and comparative examples 4, 5, carbon dioxide was used as propellant to fill up to an internal pressure of 5.5 kg/cm². In embodiments 6 and 7, liquefied petroleum gas (LPG) was used as propellant to fill up to an internal pressure of 4 kg/cm². In embodiment 8, nitrogen gas was used to fill up to an internal pressure of 7 kg/cm² at 60% filling rate.

<Test result of dispersion and re-dispersion of product>

Test results of dispersion and re-dispersion of internal liquid are shown in Table 5, in which embodiments 4 to 9 presented better dispersion and re-dispersion as compared with comparative examples 4 and 5, without being influenced by the propellant.

Figure 3:
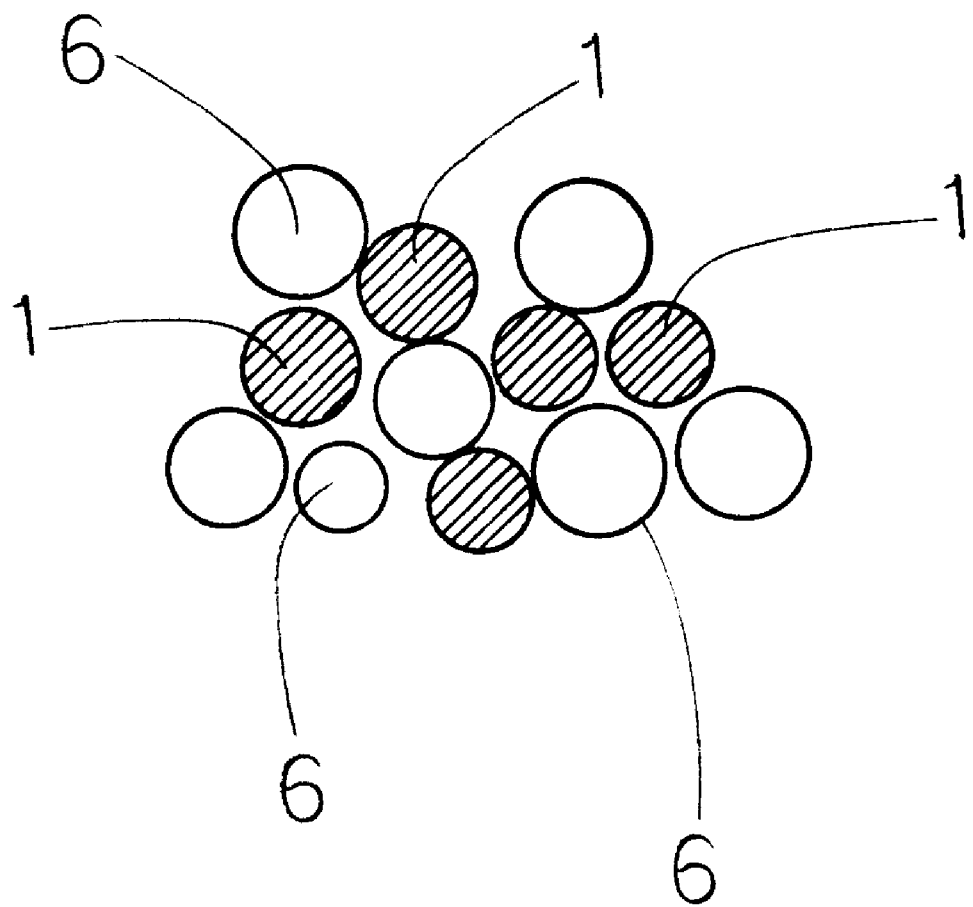
FIG. 3 is a schematic diagram showing the relation between hollow inorganic porous fine particles enveloping a chemical and synthetic resin fine particles in the invention.

As known from the test results, when silicic anhydride porous fine particles and polyethylene particles coexist in the disperse solution, frictional charging is not induced, and since both charges are negative by nature, collision between the particles can be prevented. In this case, as shown in FIG. 3, the particle size of polyethylene particles is preferred to be equal to the particle size of silicic anhydride porous fine particles 1 or larger than the particle size of silicic anhydride porous fine particles 1. This is because the behavior by the electric charge between particles should be dominant by decreasing the particle size of silicic anhydride porous fine particles which are more likely to be influenced by the pH, and increasing the particle size of polyethylene particles of organic matter which are less likely to be influenced by effect of electric charge by the pH. That is, by preventing agglutination of particles, an excellent dispersion is shown in the disperse solution.

<Testing method of prolonged action of effect (efficacy) of product>

The prolonged action of effect (efficacy) of product was tested in the same method as above.

<Test result of prolonged action of effect (efficacy) of product>

Test results of prolonged action of effect (efficacy) of product are shown in Table 5, in which embodiments 4 to 8 presented better prolonged action bf effect (efficacy) than comparative examples 4 and 5.

<Testing method of touch of product>

The touch of product was tested in the same method as above.

<Test result of touch of product>

Figure 4:
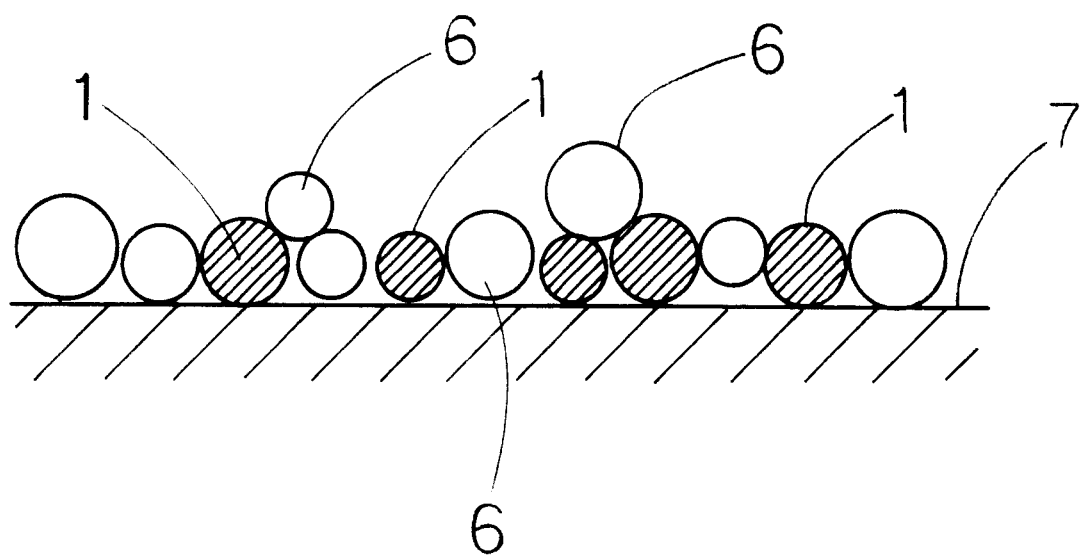
FIG. 4 is a schematic diagram showing the relation of hollow inorganic porous fine particles enveloping a chemical, synthetic resin fine particles, and the skin in the invention.

Test results of touch of product are shown in Table 5, in which embodiments 4 to 9 presented better touch on the skin as compared with comparative examples 4 and 5. In this case, as shown in FIG. 4, the particle size of polyethylene particles 6 is preferred to be equal to the particle size of silicic anhydride porous fine particles 1 or larger than the particle size of silicic anhydride porous fine particles 1. That is, same as in the case of dispersion, by preventing agglutination of particles, a dry and smooth touch is obtained, and moreover the relatively stiff feel of silicic anhydride porous fine particles 1 can be lessened by the relatively soft polyethylene particles 6.

<Test example of whitening>

An aerosol was prepared by using 50 ml of internal liquid manufactured in embodiment 5 and 50 ml of liquefied petroleum gas. By changing the type and size of silicic anhydride porous fine particles of the internal liquid, the degree of whitening was observed.

As a result, for lower degree of whitening, the maximum of particle size range should be selected at 15 microns or less, more preferably 10 microns or less, and particularly preferred results were obtained when manufactured by the surface activation method using Godball or the like.

Next, as the third internal liquid composition of the invention, two embodiments (embodiments 10 and 11) are shown below.

<Embodiment 10)

In embodiment 10, the internal liquid composition was prepared by blending as shown in Table 6, by using N,N-diethyl-m-toluamide (DEET) having a mosquito repellent effect as the chemical. The DEET was blended by carrying on silicic anhydride porous fine particles. The silicic anhydride porous fine particles were Godball E-6C of Suzuki Yushi Kogyo KK. As synthetic resin particles, polyethylene powder (Flow Peas CL-2080 of Sumitomo Seika KK) was blended, and further acrylic acid polymer was added and mixed, and moreover to give viscosity and adjust the pH, POE palm amine (tradename: Emison-45, Lion KK) was added as alkali. As other additives, concentrated glycerin, sodium POE oleyl ether phosphate (Phosphanol RO-720N of Toho Kagaku Kogyo KK), 99% denatured ethyl alcohol, and purified water were blended.

<Embodiment 11>

In embodiment 11, aluminum hydroxy chloride having an antiperspirant effect was blended as the chemical. This chemical was blended by carrying on silicic anhydride porous fine particles. The silicic anhydride porous fine particles were Godball E-6C of Suzuki Yushi Kogyo KK. As synthetic resin particles, polyethylene powder (Flow Peas CL-2080 of Sumitomo Seika KK) was blended, and further acrylic acid polymer was added and mixed, and moreover to give viscosity and adjust the pH, POE palm amine (tradename: Emison-45, Lion KK) was added as alkali. As other additives, IPM, purified water, and 99% denatured ethyl alcohol were blended.

In embodiments 10 and 11, blend compositions and test results are summarized in Table 6.

<Testing-method of dispersion and re-dispersion of internal liquid>

Dispersion and re-dispersion of internal liquid were tested in the same method as described above.

<Test result of dispersion and re-dispersion of internal liquid>

Test results of dispersion and re-dispersion of internal liquid are shown in Table 6, in which both presented excellent dispersion and re-dispersion.

<Testing method of dispersion and re-dispersion of product>

Dispersion and re-dispersion of product were tested in the same method as described above. As the propellant, carbon dioxide was used to fill up to an internal pressure of 5.5 kg/cm².

<Test result of dispersion and re-dispersion of product>

Test results of dispersion and re-dispersion of internal liquid are shown in Table 6, in which embodiments 10 and 11 presented excellent dispersion and re-dispersion.

<Testing method of prolonged action of effect (efficacy) of product>

The prolonged action of effect (efficacy) of product was tested in the same method as above.

<Test result of prolonged action of effect (efficacy) of product>

Test results of prolonged action of effect (efficacy) of product are shown in Table 6, in which embodiment 10 presented the longest prolonged action of effect (efficacy)

<Testing method of touch of product>

The touch of product was tested in the same method as above.

<Test result of touch of product>

Test results of touch of product are shown in Table 6, in which embodiments 10 and 11 presented excellent touch.

TABLE 6

| | | Third invention | |
|---|---|---|---|
| | | Embodiment 10 | Embodiment 11 |
| Inorganic porous fine particles | Godball | 3.0 (w. %) | 3.0 |
| Acrylic acid polymer | | 0.1 | 0.1 |
| Alkali | POE palm amine | 0.3 | 0.3 |
| Synthtic resin fine particles (Polyethylene powder) | | 0.6 | 0.6 |
| Active ingredient | DEET | 8.0 | |
| | Aluminum hydroxy chloride | | 0.6 |
| | Glycerin | 2.5 | |
| | IPM | | 2.0 |
| | Sodium POE oleyl ether phosphate | 2.0 | |
| Disperse solution | Purified water | 10.0 | 15.0 |
| | Ethyl alcohol | 73.5 | 73.0 |
| Propellant | | Carbon dioxide | Carbon dioxide |
| Evaluation | | | |
| Internal liquid | Particle sediment | ◎ | ◎ |
| | Particle re-dispersion | ◎ | ◎ |
| Product | Particle sediment | ◎ | ◎ |
| | Particle re-dispersion | ◎ | ◎ |
| | Prolonged action of effect | ◎ | / |
| | Dry & smooth feel | ◎ | ◎ |
| Overall effect | | ◎ | ◎ |

When the internal liquid composition of the invention is used as the internal liquid of aerosol product or spray product, the chemical ingredient carried in inorganic porous fine particles is released very slowly, and the drug effect is maintained for a long period. Moreover, the dispersion and re-dispersion of the inorganic porous fine particles carrying the chemical are improved.

In particular, the inorganic porous fine particles should be at least one kind selected from the group consisting of non-hollow porous silica spherical particles and hollow porous silica spherical particles, and the above effects are sufficiently presented by the inorganic porous fine particles of which particle size is 0.5 to 50 microns, mean particle size is 0.5 to 30.0 microns, surface pore diameter is 20 to 150 angstroms, specific surface area is 20 to 800 m²/g, and pore volume is 0.01 to 1.50 ml/g.

The disperse solution is at least one kind selected from the group consisting of alcohols and water, and when the inorganic porous fine particles are silicic anhydride porous fine particles, and the inorganic porous fine particles of which surface pore diameter is 50 to 150 angstroms occupy 40 to 90% of the total content of inorganic porous fine particles, the above effects are exhibited sufficiently.

Moreover, by blending synthetic resin particles together with inorganic porous fine particles, lowering of dispersion and re-dispersion due to effects of propellant can be prevented or suppressed, and when used on the skin, a dry and smooth touch on the skin is obtained.

In particular, by using the synthetic resin fine particles of which mean particle size is 0.1 to 50 microns, and not physically adhering with inorganic porous fine particles, lowering of dispersion and re-dispersion due to effects of propellant can be prevented or suppressed.

Further, the invention presents aerosol filling and spray products capable of exhibiting these effects.

What is claimed is:

1. An internal liquid composition contained in a releasing container as an internal liquid, comprising inorganic porous fine particles carrying a chemical, a disperse solution, and synthetic resin particles, wherein said inorganic porous fine particles are at least one kind selected from the group consisting of non-hollow porous silica spherical fine particles and hollow porous silica spherical fine particles, and the inorganic porous fine particle size is 0.5 to 50 microns, mean particle size is 0.5 to 30.0 microns, surface pore diameter is 20 to 150 angstroms, specific surface area is 20 to 800 $m^2/g$, and pore volume is 0.01 to 1.50 ml/g.

2. An internal liquid composition contained in a releasing container as an internal liquid, comprising inorganic porous fine particles carrying a chemical, a disperse solution, an acrylic acid polymer, and an alkali wherein said inorganic porous fine particles further comprise at least one kind selected from the group consisting of non-hollow porous silica spherical fine particles and hollow porous silica spherical fine particles, and the inorganic porous fine particle size is 0.5 to 50 microns, mean particle size is 0.5 to 30.0 microns, surface pore diameter is 20 to 150 angstroms, specific surface area is 20 to 800 $m^2/g$, and pore volume is 0.01 to 1.50 ml/g.

3. An internal liquid composition of claim 2, wherein the disperse solution is at least one kind selected from the group consisting of alcohols and water, the inorganic porous fine particles are silicic anhydride porous fine particles, and the inorganic porous fine particles of which surface pore diameter is 50 to 150 angstroms occupy 40 to 90% of the total content of inorganic porous fine particles.

4. A releasing container product having an internal liquid and a propellant contained and enclosed in a pressure-proof container for aerosol, wherein the internal liquid is composed in the internal liquid composition in claim 2.

5. A releasing container product having an internal liquid contained in container having a releasing mechanism by pump spray, wherein the internal liquid is composed in the internal liquid composition in claim 2.

6. An internal liquid composition contained in a releasing container as an internal liquid, comprising inorganic porous fine particles carrying a chemical, a disperse solution, and fine particles for dispersion made of a different material from the inorganic porous fine particles, wherein the fine particles for dispersion have a surface electric charge of the same positive (+) or negative (−) polarity as the surface electric charge of the inorganic porous fine particles, and when the fine particles for dispersion are mixed in the group of the inorganic porous fine particles, collision between inorganic porous fine particles is prevented.

* * * * *